US00PP09715P

United States Patent [19]

Carruth

[11] Patent Number: Plant 9,715

[45] Date of Patent: Dec. 3, 1996

[54] SHRUB ROSE PLANT NAMED 'WEKPLASOL'

[75] Inventor: Thomas F. Carruth, Altadena, Calif.

[73] Assignee: Weeks Wholesale Rose Grower, Inc., Upland, Calif.

[21] Appl. No.: 561,396

[22] Filed: Nov. 21, 1995

[51] Int. Cl.[6] ..... A01H 5/00

[52] U.S. Cl. ..... Plt./1

[58] Field of Search ..... Plt./1

*Primary Examiner*—Howard J. Locker

*Attorney, Agent, or Firm*—Christie, Parker & Hale, LLP

[57] ABSTRACT

A new variety of Shrub rose suitable for garden decoration, having flowers of yellow, peach and pink coloration.

1 Drawing Sheet

BACKGROUND OF THE INVENTION

This invention relates to a new and distinct variety of Shrub Rose. The varietal denomination of the new variety is 'Wekplasol'. The plant is a upright spreading seedling cultivated for outdoor garden decoration. It has as its seed parent the variety known as 'Playboy' and an undisseminated seedling as its pollen parent.

SUMMARY OF THE INVENTION

Among the features which distinguish the new variety from other presently available and known commercial rose cultivars are the following combination of characteristics: its large pyramidal clusters of single flowers, its blushed flower colors that give a multi-color effect, its highly glossed deep green foliage, and its unusually strong vigor and good disease resistance. 'Wekplasol' may be asexually propagated by cuttings, budding, or grafting.

Asexual reproduction of the new variety by cuttings and budding as performed in Kern County and Upland, Calif. shows that the foregoing and other distinguishing characteristics come true to form and are established and transmitted through succeeding propagations.

COMPARISON WITH PARENTS

The new rose may be distinguished from its seed parent, 'Playboy', by the following combination of characteristics: whereas 'Playboy' bears large single flowers of a blended orange and yellow coloration, 'Wekplasol' bears significantly smaller flowers that blush to differing shades. The seed parent has a medium sized plant habit and is classed as a Floribunda, whereas the new variety has a much larger plant habit and is classed as a Shrub. 'Wekplasol' mostly bears its flowers in large pyramidal clusters, whereas 'Playboy' bears flowers in significantly smaller clusters.

The new variety may be distinguished from its pollen parent, an undisseminated seedling, by the following combination of characteristics: whereas the pollen parent bears semi-double flowers of a clear yellow coloration, 'Wekplasol' bears single flowers with fewer petals that blush to differing shades. The pollen parent has medium-sized foliage with a matte finish, whereas the new variety has smaller foliage with a very glossy finish.

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout the description, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Upland, Calif. in the month of September. Phenotype expression may vary with environmental, cultural and climatic conditions, as well as differences in conditions of light and soil.

Flower

The new variety usually bears its flowers in clusters of several per stem. Flowers are borne in regular pyramidal clusters on strong long stems (about 30 to about 42 cm). Outdoors, the plant blooms very freely and nearly continuously during the growing season. The flowers have a moderate, sweet, apple-like fragrance.

Bud

The peduncle is of average length for the class (about 3.5 to about 5.5 cm), and usually erect. It is almost entirely smooth, with very few stipitate glands and some small hairs. Peduncle color is between 144A and 138A, sometimes moderately suffused on the side facing the sun with between 183A and 187A.

Before the calyx breaks, the bud is of small to medium size (about 1.5 to about 2 cm in diameter at the widest point), mediun in length (about 2.5 to about 3.5 cm), and very pointed in shape with a conspicuous globular hypanthium. The surface of the bud is almost entirely smooth, with very few stipitate glands and some small hairs, usually with slender foliaceous parts extending beyond the tip of the bud equal to about ½ or more of its length. Bud and hypanthium color is between 144A and 138A, sometimes moderately suffused on the side facing the sun with between 183A and 187A.

The inner surface of the sepals is covered with fine wooly tomentum; sepal margins are lined with few stipitate glands and some hairs.

As the petals open, the bud is small to medium size (about 1.8 to about 2.3 cm in diameter at the widest point), medium in length (about 2.7 to about 3.5 cm), and very pointed in form. The color of the under surfaces of the newly opened petals is between 14A and 13B, often tipped and blushed with between 46A and 46C. The color of the upper surfaces of the newly opened petals is between 14A and 13B. The bud opens well and is not prevented from opening by wet, cold, hot or dry weather.

Bloom

When fully open, the bloom is medium sized for the class, ranging from about 6 to about 7 cm in diameter. Petalage is single with about 5 petals and arranged regularly. When partially open, the bloom form is more cupped to flat, and the petals are cupped to undulated. When fully open, the bloom form is flattened.

Petals

The substance of the petals is moderately heavy and of medium thickness, with upper surfaces slightly satiny and under surfaces slightly shiny. The petals are moderately round to broadly obovate in shape with rounded apices.

Newly Opened Flower

On the first day of opening, the under surface of the petals is between 13B and 12A, sometimes tipped and blushed with between 46B and 45C. The upper surface of the petals is between 13B and 12A.

The general tonality of the newly opened flower on the first day is between 13B and 12A.

On the second-day of opening, the under surface of the petals is between 12B and 12C, often lightly suffused toward the outermost portion of the petal with between 43C and 39B. The upper surface of the petals is between 12B and 12C, with some suffusion of between 44D and 39B.

The general tonalith of the second day open flower is between 12B and 12C, lightly blushed with between 44D and 39B.

Mature Open Flower

On the third-day of opening, the under surface of the petals is between 12C and 12D, suffused toward the outermost portion of the petal with between 43C and 39B. The upper surface of the petals is between 12C and 12D, heavily suffused over the majority of the petal with between 44D and 39B.

The general tonality of the third day open flower is between 12B and 12C, heavily blushed with between 44D and 39B.

On the fourth day of opening, the under and upper surface of the petals is between 18C and 19D, often irregularly suffused with near 45C.

The general tonality of the four day old flower is between 18C and 19D, irregularly suffused with near 45C.

The petals usually drop off spent bloom cleanly.

In September, in Upland, Calif., blooms on the bush growing outdoors generally last about four days. Cut roses grown outdoors and kept at normal indoor living temperatures generally last about four days.

Male Reproductive Organs

Stamens are average to many in number and are arranged regularly about the pistil. The filaments are of irregular length, most with anthers. The anthers are of medium size and all open approximately at the same time. Anther color is near 14A when immature and near 16B at maturity. Pollen is very abundant and near 12D in color.

Female Reproductive Organs

Pistils vary in number but usually number about b 40. The styles are moderately even, average in length, average in caliper, and somewhat bunched. Stigma color is near 8B. Style color is near 4D, lightly suffused with near 36D. Ovaries are usually all enclosed in the calyx.

Hips have not been observed on this variety when grown in Upland, Calif.

Foliage

The compound leaves are usually comprised of three to five or more leaflets and are borne abundantly. The leaves are medium in size (about 8 to about 10 cm in length and about 7 to about 8.5 cm in width at the widest point), moderately heavy to leathery in texture, and very glossy in finish. The leaflets are medium in size (about 3.5 to about 6 cm in length and about 2.5 to about 3.5 cm in width at the widest point), shaped somewhat oval to ovate with moderately acute apices and somewhat round to acute bases. The margins are usually simply serrate.

The upper surface of the mature leaf is between 137A and 147A. The under surface of the mature leaf is between 147B and 191 A. The upper surface of the young leaf is between 144A and 137A, usually suffused more at the very edge of the leaf with between 183A and 187A. The under surface of the young leaf is near 147B, usually moderately suffused with between 183A and 187A.

The rachis is average in caliper. The upper side is somewhat shallowly grooved and very smooth with very few stipitate glands and some hairs. The under side of the rachis is very smooth with some hairs and few stipitate glands.

The stipules are medium to long in length with somewhat narrow width with medium long straight points that usually turn out at an angle of more than 45 degrees. The stipules are edged with many stipitate glands.

The plant displays an above average degree of resistance to powdery mildew and rust as compared to other commercial varieties grown under comparable conditions in Upland, Calif.

Growth

The plant has a bushy, upright-spreading, tall habit (about 190 to about 250 cm in height and about 150 to about 180 cm spread at the widest point), with very full branching. It displays very vigorous growth and the canes are of medium to heavy claiper for the class.

The color of the major stems is near 144C. They bear a few large prickles which are of medium length (about 0.8 to about 1.2 cm long). The large prickles are almost straight and angled slightly downward with a medium length to moderately narrow base; prickle color is near 165A. The major stem bears no small prickles.

The color of the branches is between 144A and 138A, often suffused on the side exposed to sun with near 165A. They bear a few large prickles which are of medium length (about 0.8 to about 1.2 cm long). The large prickles are almost straight and angled slightly downward with a medium length to moderately narrow base; prickle color is near 165B. The branches bear very few small prickles of similar shape and coloration.

The color of the new shoots is between 144B and 138B, often heavily suffused on the side exposed to sun with near 187A. They bear a few large prickles which are of medium length (about 0.8 to about 1.2 cm long). The large prickles are almost straight and angled slightly downward with a medium length to moderately narrow base; prickle color is between 183A and 187A. The shoots bear a few small prickles of similar shape and coloration.

I claim:

1. A new and distinct variety of shrub rose plant substantially as described and illustrated herein.

* * * * *

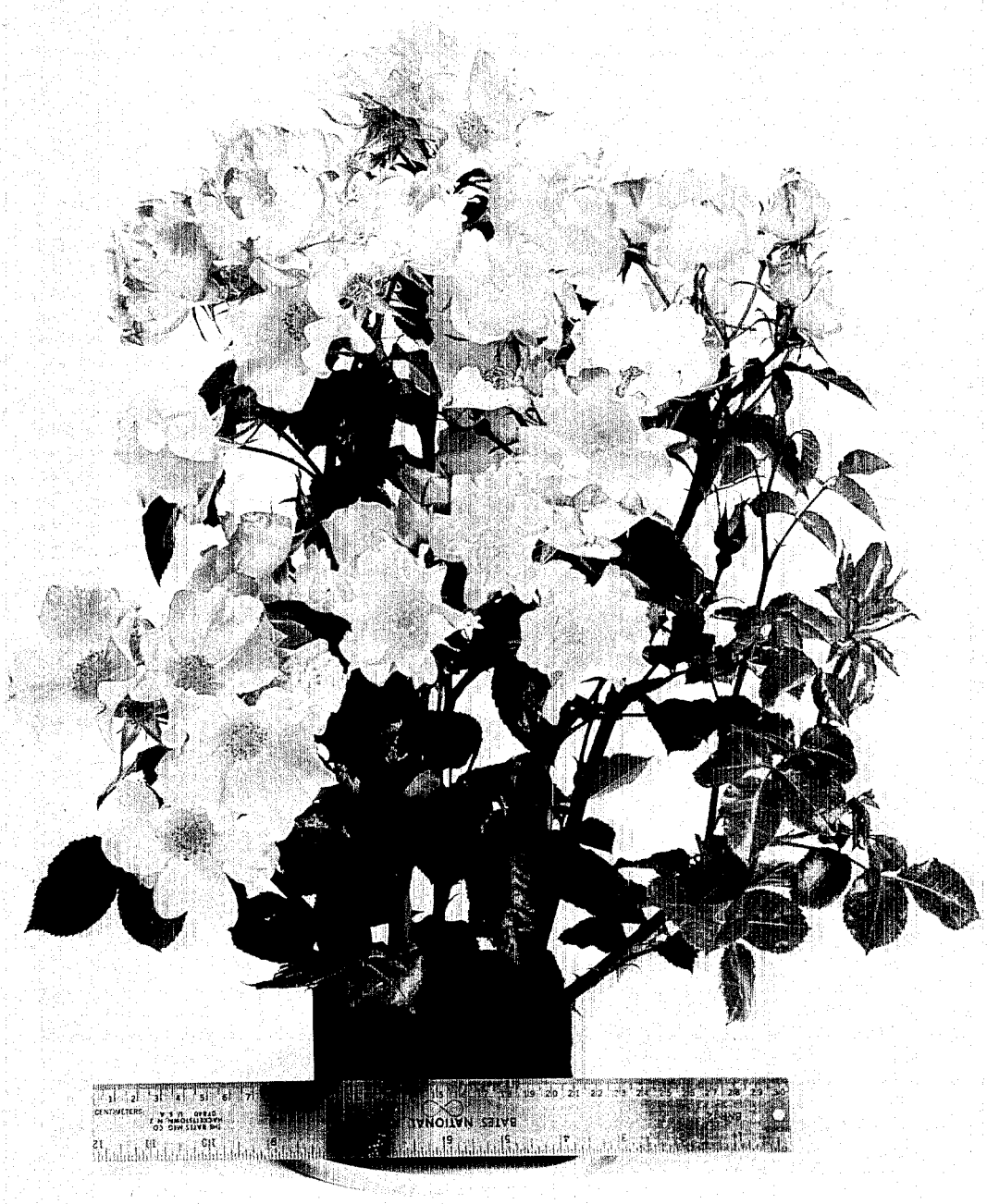
BATES NATIONAL
CENTIMETERS

UNITED STATES PATENT AND TRADEMARK OFFICE

CERTIFICATE OF CORRECTION

PATENT NO. : Plant 9,715
DATED : December 3, 1996
INVENTOR(S) : Thomas F. Carruth It is certified that error appears in the above-indentified patent and that said Letters Patent is hereby corrected as shown below:

Column 3, line 33, change "tonalith" to -- tonality --.
Column 3, line 66, change "16B" to -- 165B --.
Column 4, line 3, change "b40" to -- 40 --.
Column 4, line 49, change "claiper" to -- caliper --.

Signed and Sealed this

Twenty-sixth Day of August, 1997

*Attest:*

Bruce Lehman

BRUCE LEHMAN

*Attesting Officer*

*Commissioner of Patents and Trademarks*